United States Patent
Pöchmüller et al.

(10) Patent No.: US 7,274,386 B2
(45) Date of Patent: Sep. 25, 2007

(54) METHOD FOR DETERMINING VISIBILITY

(75) Inventors: Werner Pöchmüller, Hildesheim (DE); Goetz Kuehnle, Hemmingen (DE)

(73) Assignee: Robert Bosch GmbH, Stuttgart (DE)

( * ) Notice: Subject to any disclaimer, the term of this patent is extended or adjusted under 35 U.S.C. 154(b) by 476 days.

(21) Appl. No.: 10/333,230

(22) PCT Filed: May 25, 2001

(86) PCT No.: PCT/DE01/02028

§ 371 (c)(1),
(2), (4) Date: Aug. 12, 2003

(87) PCT Pub. No.: WO02/06851

PCT Pub. Date: Jan. 24, 2002

(65) Prior Publication Data

US 2004/0046866 A1    Mar. 11, 2004

(30) Foreign Application Priority Data

Jul. 15, 2000 (DE) .............................. 100 34 461

(51) Int. Cl.
*H04N 7/18* (2006.01)
(52) U.S. Cl. ...................................... 348/135
(58) Field of Classification Search ............... 348/135, 348/136, 137, 145, 144, 150; 382/107, 104, 382/103; 356/338, 339; *H04N 1/18*
See application file for complete search history.

(56) References Cited

U.S. PATENT DOCUMENTS

| | | | |
|---|---|---|---|
| 4,216,498 A | | 8/1980 | Evans et al. |
| 4,921,349 A | | 5/1990 | Richards |
| 5,109,425 A | * | 4/1992 | Lawton ................ 382/107 |
| 5,987,152 A | * | 11/1999 | Weisser ................ 382/104 |
| 6,108,084 A | * | 8/2000 | Winner ................ 356/338 |
| 6,362,773 B1 | * | 3/2002 | Pochmuller .......... 342/52 |
| 6,840,342 B1 | * | 1/2005 | Hahn ................. 180/169 |

FOREIGN PATENT DOCUMENTS

| | | |
|---|---|---|
| DE | 3801 368 | 7/1989 |
| DE | 195 30 289 | 2/1997 |
| DE | 196 40 938 | 4/1998 |
| DE | 199 28 915 | 1/2001 |
| EP | 0 687 594 | 12/1995 |
| EP | 0 691 534 | 1/1996 |
| JP | 63 188741 | 8/1988 |

OTHER PUBLICATIONS

EP-Literatur 1 "Visibiilty estimation from a moving vehicle using the Ralph vision system" XXPO10270909.

* cited by examiner

*Primary Examiner*—Tung Vo
(74) *Attorney, Agent, or Firm*—Kenyon & Kenyon LLP

(57) ABSTRACT

To determine the visual range of, in particular, a driver in a motor vehicle, a contrast $((c(x_1), c(x_2))$ is measured from at least two measuring positions $(x_1, x_2)$ of a measuring device situated at different distances from the object, and the ratio of the measured contrast values is converted to a visual range $(\delta)$, using the difference of the distances of the measuring positions from the object.

18 Claims, 3 Drawing Sheets

Figure 2:
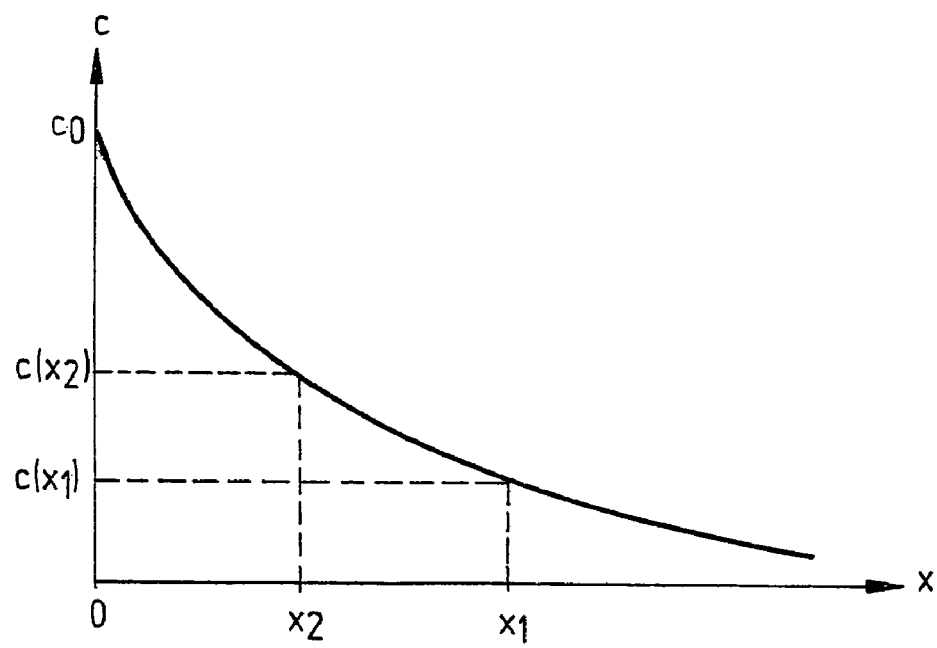

Fig.1a
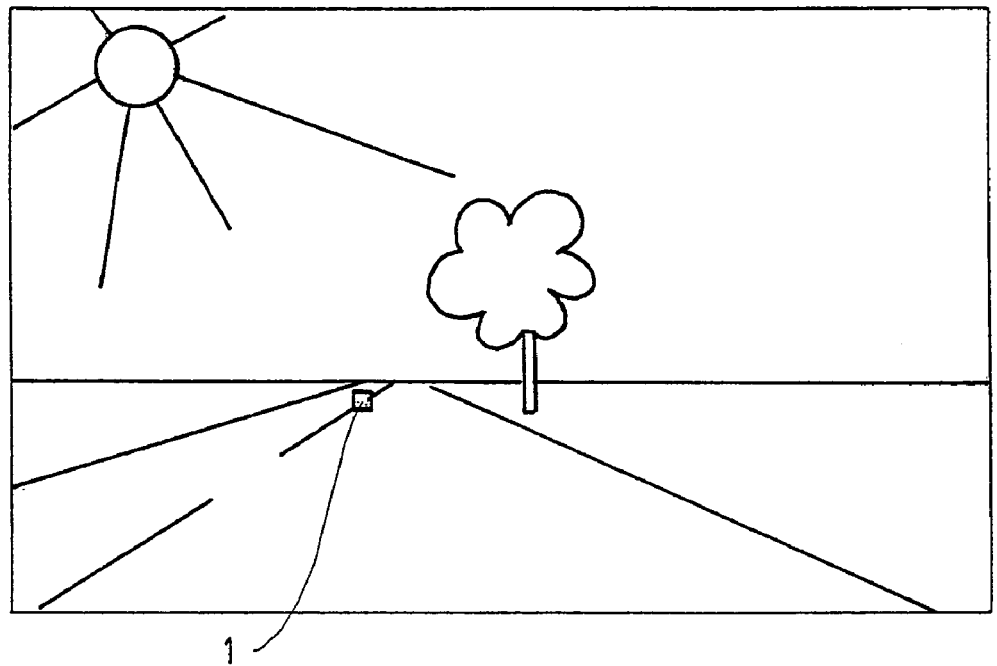
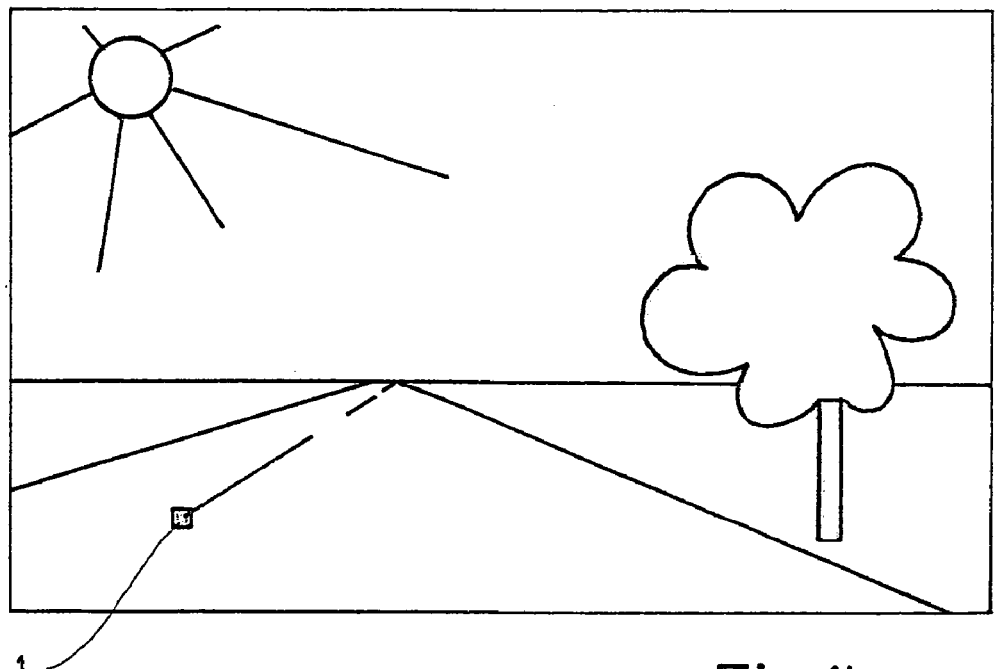
Fig.1b

METHOD FOR DETERMINING VISIBILITY

BACKGROUND INFORMATION

The determination of the visual range in a turbid medium, i.e. the determination of a range, outside of which two separate or different-colored objects are no longer reliably distinguishable to an observer, is a technical problem that is particularly relevant to the control of vehicles, since the visual range substantially determines the maximum safe speed that may be traveled. The multitude of accidents occurring per year under conditions of limited sight distance, e.g. in the case of fog, indicates that it is very difficult for a human driver to quantitatively determine the current visual range and adjust the speed of his or her vehicle to this visual range.

Therefore, it is desirable to be provided with methods for measuring the visual range, which can be used, for example, in future driver assistance systems, in order to supply, in each case, a warning signal in response to a maximum speed set as a function of the measured visual range being exceeded, and thus to cause the driver to reduce his speed. Quantitative determination of the visual range is also of particular importance in future driver assistance systems that take away parts of the driving tasks of the driver, such as the longitudinal vehicle control system (automatic gasoline/brake intervention in an adaptive driving-speed control system.

Two different types of visual ranges are of principle interest. In this context, the first is the objective visual range (standard visual range), which is given by the attenuation of an optical signal in response to penetrating a certain segment of the medium in which the visual range is to be measured.

Secondly, one would like to determine the subjective visual range of the driver. This is influenced by factors such as external lighting, contrasts, surroundings, the size of surrounding objects, as well as the individual visual acuity of the driver. When driving, for example, at night in nonilluminated surroundings, the subjective visual range of the driver is therefore limited to the boundary of the vehicle-headlight cones. But if one is driving at night on an illuminated avenue, then the visual range is considerably larger. In both cases, the attenuation of a light signal in the atmosphere, and thus the standard visual range, are the same. Due to the multitude of possible environmental effects and individual parameters, it is considerably more difficult to determine the subjective visual range than the objective visual range, i.e. it is only possible to a limited extent.

Techniques for measuring the standard visual range are being tested for use in motor vehicles. These are essentially active methods, which operate according to the backscattering principle. In this context, an optical signal is emitted into the medium to be measured. The optical signal scattered back is picked up by an appropriate sensor, and the transmittance of the medium with respect to the emitted signal is deduced by analyzing the time characteristic of the received signal. In order to prevent the driver from being disturbed by the measurement during use in a motor vehicle, an optical signal in the near-infrared range must be used.

Since active methods generally work with their own light source, they are limited to the determination of the standard visual range. The lighting conditions actually perceived by the driver cannot be taken into consideration. Since the subjective visual range perceived by the driver cannot be larger than the standard visual range, but is often considerably smaller, the suitability of these methods for use in driver-assistance systems is very limited.

Besides the active methods mentioned, passive methods, which only work with the light already present in the environment, are also proposed. An example of such a passive method and a device for implementing it is referred to in EP 0 687 594 B1. In the method known from this document, a camera is used to generate an image of a field of view, and the number of black and white pixels in the image is compared to a limiting value. The result of the method is the statement that fog is present when the limiting value is not reached, or that no fog is present when the limiting value is exceeded.

Therefore, this known method only allows a rough estimation. A quantitative measurement of the visual range is not possible, since, during the evaluation of the image generated by camera, no information is present as to which objects the image contains and which contrasts these have by nature. Therefore, the known method can conclude that fog is present, when the field of view is mostly filled in with objects having little contrast.

SUMMARY OF THE INVENTION

In contrast, the method of the present invention has the advantage, that it allows a quantitative determination of the visual range and is independent of the actual contrast values of the objects on which the measurement is carried out.

These advantages are attained by measuring the contrast at an object from at least two measuring positions situated at different distances from the object, and converting the change in the measured contrast values to a visual range. When the air in the path from the object to the two measuring positions becomes measurably hazy, this causes a lower contrast to be measured in the further removed measuring position than in the one less distant. In this context, the relative degree of the change in contrast is unexpectedly independent of the actual contrast of the object, so that it is possible to quantitatively convert the change in the measured contrast values to a visual range, when the distances of the two measuring positions from the object are known.

According to a first embodiment of the method, the distance of the measuring device from the object is measured absolutely at each measuring position, preferably using optical methods such as triangulation.

However, only the knowledge of the difference of the measuring-position distances from the object is generally sufficient for the conversion.

When the method of the present invention for measuring the visual range of a driver is used in a moving motor vehicle, the difference of the distances may be equated to the distance traveled by the motor vehicle between the two measuring positions.

This distance traveled by the motor vehicle may be determined in a simple manner, using a speed signal present in the vehicle and a time reference.

Alternatively, the distance traveled may also be determined by measuring the angle of rotation of a vehicle wheel covered between the measuring positions.

In each instance, the object whose contrast is measured is advantageously selected inside a conical volume having a predetermined opening angle; in each case, the vehicle being at the vertex of the cone and the direction of movement of the vehicle corresponding to the axis of the cone. The opening angle results from compromise between the requirements that, on one hand, a large opening angle of the cone makes it easier to find a high-contrast object well-suited for the measurement, but on the other hand, the closer the selected object to the axis of the cone, the lesser the accuracy of the measurement is affected by parallel-axis errors.

Since the knowledge of the visual range in the direction of travel is of particular interest to the driver of a motor vehicle, it is useful in most cases to select the object in a conical volume, which is situated in front of the vehicle in the direction of travel.

However, it can also prove to be advantageous to select the object in a conical volume that is behind the vehicle in the direction of travel. This procedure has the advantage that, at the time at which the object is selected, it is at a short distance from the vehicle, in which the contrast measurable from the vehicle is relatively high. This contrast fades with increasing distance. Therefore, the second measurement may be conducted at a relatively long distance, which is essentially limited by the capability of an image-analysis system connected to the measuring device, of tracking the selected object. When measuring in the direction of travel, there is, however, the problem that, among the several low-contrast objects that may be selected at the time of the first measurement, it is not known, which of these is far away from the vehicle and objectively high-contrast and therefore represents a suitable test object.

The problem of finding a suitable object for measuring the contrast particularly occurs, when the visual range is actually limited by fog or the like. In the case of good visibility or visibility that is more or less good, it may therefore prove useful to select, in each instance, a target in the direction of travel, and, if the failure of measurements in the direction of travel indicates poor visibility, to use a target in the direction opposite to the direction of travel.

The same advantageous effect may also be achieved in the case of selecting an object in the direction of travel, in that an image is recorded at each of the two measuring positions, the object in the most recent of the images is selected as it is automatically the largest and has the sharpest contrast, and it is identified in the at least one older image in order to conduct the contrast measurement.

In order to further improve the measuring accuracy, the contrast measurement at the object may also be carried out from three or more measuring positions that are at different distances from the object, and the visual range is determined by an adaptation method, such as the method of error squares, for instance.

A measuring device having a CCD or CMOS image sensor as a spatially-resolving, image sensor is preferably used to implement the method. In the case of such an image sensor, an object suitable for a contrast measurement may be selected by calculating a gradient of the measured light intensity over the image surface of the sensor and selecting a region having a high gradient.

A nonlinear, preferably logarithmic, varying characteristic of the image sensor simplifies the evaluation of the recorded images.

Further features and advantages of the present invention are derived from the following description of exemplary embodiments, with reference to the figures.

FIGURES

Figure 3:
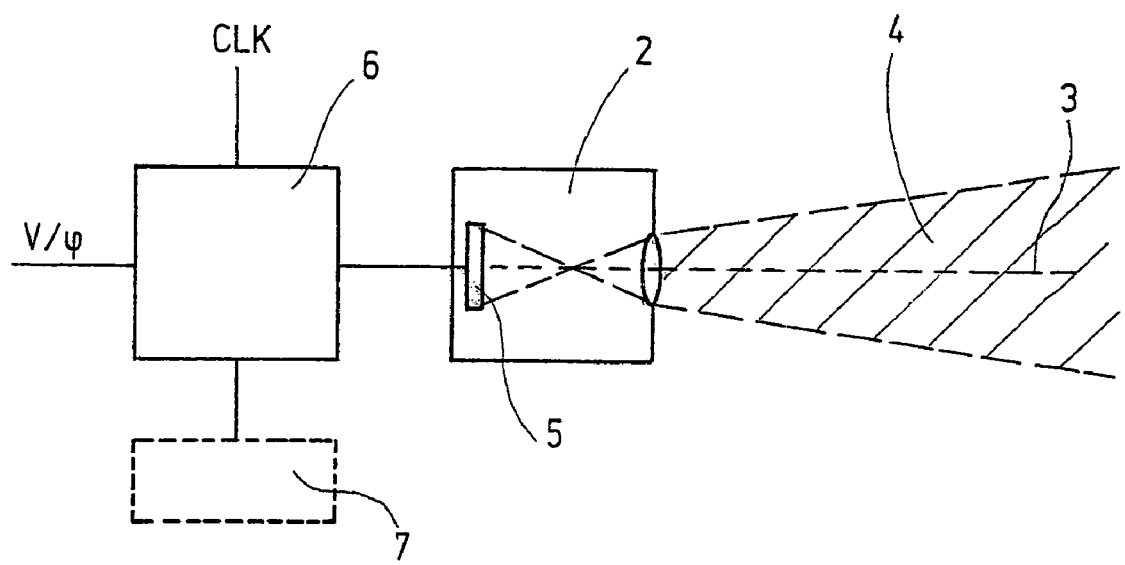
Figure 4:
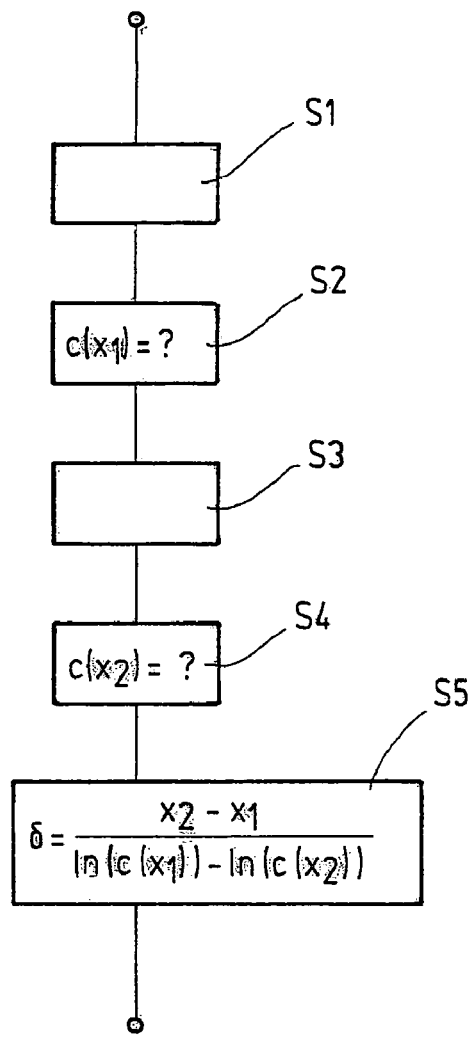

The figures show:

FIGS. 1a, 1b a typical application situation of the method according to the present invention;

FIG. 2 the apparent contrast of an object as a function of the distance between the object and the measuring device;

FIG. 3 a schematic of a measuring device for implementing the method of the present invention;

FIG. 4 a flow chart of a first embodiment of the method; and

Figure 5:
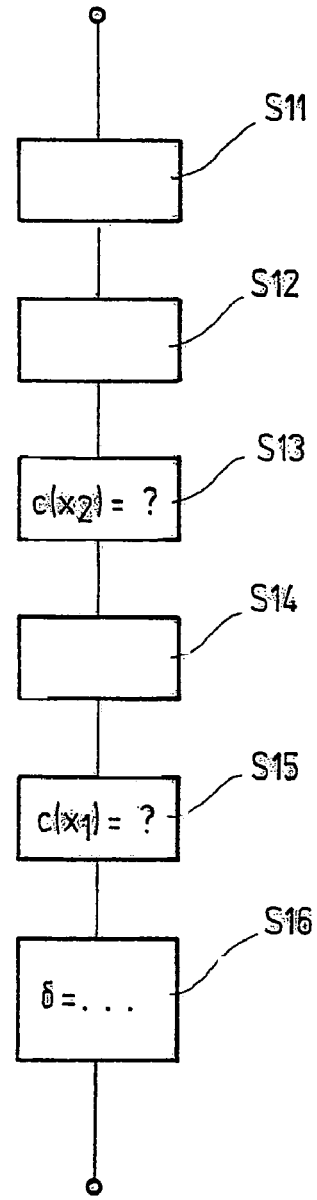

FIG. 5 a flow chart of a second embodiment of the method.

DESCRIPTION OF THE EXEMPLARY EMBODIMENTS

Parts a and b of FIG. 1 show a typical traffic scene from the point of view of the driver of a motor vehicle, as seen in the direction of travel. The scene is represented at two different times $t_1$ and $t_2$, $t_2$ being later than $t_1$. The corner of a lane marking having a pronounced bright-dark contrast is selected here as an object 1 for a contrast measurement. The object is detected and measured in the image of a camera at time $t_1$. It is then tracked in the image over a certain time interval, and the contrast is measured again at a later time $t_2$.

Under optimum visibility conditions, the results of the contrast measurements should be equal at times $t_1$ and $t_2$. When visibility is poor, e.g. because of fog, rain, smoke, or the like, the contrast at time $t_2$ should be greater than that of time $t_1$. Even in darkness, it should be assumed that the contrast of object 1 increases as it moves closer to the headlights of the vehicle.

FIG. 2 shows the apparent contrast of object 1 measurable from the vehicle, as a function of distance x. When distance x=0, the measured contrast is equal to the actual or objective contrast $c_0$, i.e. the contrast directly on the surface of the object. Apparent contrast c, i.e. the contrast that is measurable from a distance and is affected by the turbidity of the atmosphere, decreases with increasing distance according to the formula $$c(x)=c_0 e^{-x/\delta}$$

where $\delta$ may be defined as the visual range. As one can easily derive from the above formula, visual range $\delta$ may be determined as follows, using two measurements of contrast at arbitrary distances $x_1$ and $x_2$ from object 1.

$$\delta = \frac{x_2 - x_1}{\ln(c(x_1)/c(x_2))} = \frac{x_2 - x_1}{\ln(c(x_1)) - \ln(c(x_2))}$$

Therefore, the measured value obtained for visual range $\delta$ is completely independent of real contrast $c_0$. Consequently, no information at all about the type of object selected for the measurement is necessary to correctly evaluate the measured contrast values.

FIG. 3 shows a highly schematic block diagram of the device for implementing the method according to the present invention. The device includes a camera 2, whose optical axis 3 is aligned in a direction essentially parallel to the direction of travel of the vehicle. The field of view of the camera defines a conical volume 4, which is represented in the figure as a hatched surface. For example, camera 2 may be situated in a front or rear bumper of the vehicle, or in the immediate vicinity of a headlight. Positioning the camera near the headlight has the additional advantage that the field of view of the camera may largely coincide with the light cone of the headlight, which makes it easier to measure the subjective visual range of the driver in the dark.

The camera includes, as an image-recording element, a CCD or CMOS sensor 5 having a multitude of pixels arranged to form a matrix of lines and columns. The pixels have a nonlinear varying characteristic.

According to a first variant, this characteristic may be adapted to the light sensitivity of the human eye, so that the signal provided by each individual pixel is proportional to the brightness value perceived by a human eye for the corresponding pixel.

A second variant provides for the pixels having a logarithmic varying characteristic. This variant simplifies the measurement of contrast, since the contrast between two points of an object that are of different brightness, i.e. the ratio of the light intensities emitted by these two points, corresponds to the difference of the signals supplied by the corresponding pixels of image sensor 5. This means that, in a processing circuit connected to the image sensor 5 having a logarithmic varying characteristic, the measurement of a contrast only requires the calculation of a difference, not a computationally time-intensive division.

In the device of FIG. 3, a processing unit 6 is connected to image sensor 5 and receives images from it.

The processing of the images in processing unit 6 may be accomplished in different ways. The first step of a first method represented in FIG. 4 provides for the selection of an object in an image (S1) provided by image sensor 5, and a measurement of contrast $c(x_1)$ of object (S2), the distance $x_1$ between the camera and the object not being known at this time. In subsequent step S3, the object is tracked for a while in images supplied by image sensor 5 in rapid succession, while the vehicle continues to move. Subsequent step S4 includes the re-measuring of a contrast value $c(x_2)$ of the object. Distance $(x_1-x_2)$ covered by the vehicle during the tracking of the object is determined by the computing circuit, by integrating a speed signal over time with the aid of an external timing signal CLK, the speed signal being supplied, for example, by the vehicle speedometer. The distance may also be determined by tracking the change in an angle-of-rotation signal $\Phi$ read off at a wheel of the vehicle, between the two measurements. Visual range $\delta$ is then calculated according to the above-mentioned formula.

This "elementary" variant of the method may be refined in many respects. An example of one possibility is to measure not only two contrast values for the selected object, but rather several contrast values, so that the curve shown in FIG. 2 may be fitted by the method of least squares, using a plurality of measuring values, and in this manner, $\delta$ may be determined with high accuracy.

In each image supplied by image sensor 5, it is also possible to select not just one object, but rather to take contrast measurements at several objects, in order to thus be provided with several measured values of visual range $\delta$ recorded at each different object.

In order to find objects suitable for a measurement, processing unit 6 must ascertain the regions of an image delivered by sensor 5, which reach a predetermined, minimum contrast.

If the vehicle is actually moving through fog, objects may only attain this minimum contrast as of a short distance from the vehicle. Then, the first contrast measurement may only be conducted at a short distance from the vehicle, and the time for a second measurement may become short, so that many measuring attempts may fail. This problem may be countered by not orienting the field of view of camera 2 in the direction of travel, but rather in the direction opposite to the direction of travel, or better yet, by assigning processing unit 6 two cameras, of which one is pointed in the direction of travel and the other in the opposite direction, so that, if measurements in the direction of travel become difficult, processing unit 6 may switch over to measurements made with the aid of camera oriented in the direction opposite to the direction of travel. For, in order to measure contrast, the camera oriented in the direction opposite to the direction of travel selects, in each instance, the highest-contrast object from all of the objects in its field of view, since this object is the one that remains visible the longest and remains suitable for a measurement, even as the distance of the vehicle from the object, increases.

According to an advantageous further refinement, processing unit 6 is assigned an image memory 7, which is represented by a dotted line in FIG. 3 and is used to buffer images supplied by image sensor 5 for a limited time span. The method implemented by this further-developed device is explained with reference to FIG. 5.

In step S11, an image supplied by image sensor 5 is initially temporarily stored in image memory 7 without additional processing. After the vehicle has covered a given distance and image sensor 5 has supplied a new image, an object suitable for measuring contrast is selected (step S12) in this newer image, and its contrast is measured (step S13).

This object may be the highest-contrast region of the new image, i.e. the measurement of the contrast may also precede the selection of the object. In particular, the object of highest contrast may be determined with a small amount of computing expenditure, when an image sensor 5 having a logarithmic varying characteristic is used.

Contrast $c(x_2)$ of the object is temporarily stored, and, in step S14, the selected object is identified in the older image. This identification may also be accomplished by retracing the object with the aid of several images that are likewise recorded and temporarily generated in image memory 7; however, cross-correlation techniques may also be used.

After the object is detected in the older image, its contrast $c(x_1)$ is determined in this image (step S15), and the visual range is calculated as indicated above (step S16).

In addition, this method may easily be used in the case of small visual ranges, because the object selected in the newer image may also be identified in the older image in a simple manner, when it only has a very small contrast.

In this embodiment of the method, it is also possible, of course, to simultaneously conduct measurements at a plurality of objects, or to generate and evaluate more than two measured contrast values for an object.

What is claimed is:

1. A method for determining a visual range, comprising:
   in order to produce measured contrast values, measuring a contrast at an object from at least two measuring positions of a measuring device situated at different distances from the object; and
   converting a change in the measured contrast values to the visual range;
   wherein the visual range is determined according to the following relationship:

$$\delta = \frac{x_2 - x_1}{\ln(c(x_1)/c(x_2))} = \frac{x_2 - x_1}{\ln(c(x_1)) - \ln(c(x_2))}$$

wherein $\delta$ denotes the visual range, $x_1$ and $x_2$ are distances of the at least two measuring positions from the object, and c denotes contrast.

2. The method as recited in claim 1, wherein:
   the converting is performed in accordance with a ratio of the measured contrast values and a difference of the distances of the at least two measuring positions from the object.

3. The method as recited in claim 1, wherein:
the method is used for measuring the visual range of a driver in a moving motor vehicle.

4. The method as recited in claim 1, wherein:
a distance of the measuring device from the object is measured absolutely at each measuring position using triangulation.

5. The method as recited in claim 3, further comprising:
determining a difference of the distances of the at least two measuring positions from the object by measuring a distance traveled by a motor vehicle between the at least two measuring positions.

6. The method as recited in claim 5, further comprising:
calculating a distance traveled by the motor vehicle in accordance with a speed signal present in the motor vehicle and a time reference.

7. The method as recited in claim 5, further comprising:
determining a distance traveled by the motor vehicle by measuring an angle of rotation covered by a vehicle wheel between the at least two measuring positions.

8. The method as recited in claim 3, wherein:
in each instance, the object is selected within a conical volume that has a predefined opening angle and at whose apex the motor vehicle is located, an axis of the conical volume corresponding to a direction of movement of the motor vehicle.

9. The method as recited in claim 8, wherein:
the conical volume is situated in front of the motor vehicle in a direction of travel.

10. The method as recited in claim 8, wherein:
the conical volume is situated in back of the motor vehicle in a direction of travel.

11. The method as recited in claim 8, wherein:
the conical volume is situated in back of the motor vehicle in a direction of travel, when a visual-range measurement at another object situated in front of the motor vehicle in the direction of travel fails.

12. The method as recited in claim 8, further comprising:
in order to conduct a contrast measurement, initially recording an image at each of the at least two measuring positions to produce images; and
subsequently selecting the object in a most recent of the images, and thereafter identifying the object in at least one older one of the images.

13. The method as recited in claim 1, further comprising:
conducting a contrast measurement at the object from at least three measuring positions situated at different distances from the object; and
determining the visual range using a fitting operation.

14. The method as recited in claim 1, wherein:
at least one of the measured contrast values obtained for the visual range is used for setting a maximum speed of a motor vehicle.

15. A measuring device for determining a visual range, comprising:
an arrangement, in order to produce measured contrast values, for measuring a contrast at an object from at least two measuring positions of a measuring device situated at different distances from the object;
an arrangement for converting a change in the measured contrast values to the visual range; and
one of a CCD image sensor and a CMOS image sensor;
wherein the visual range is determined according to the following relationship:

$$\delta = \frac{x_2 - x_1}{\ln(c(x_1)/c(x_2))} = \frac{x_2 - x_1}{\ln(c(x_1)) - \ln(c(x_2))}$$

wherein $\delta$ denotes the visual range, $x_1$ and $x_2$ are distances of the at least two measuring positions from the object, and c denotes contrast.

16. The measuring device as recited in claim 15, wherein:
the one of the CCD image sensor and the CMOS image sensor includes a nonlinear varying characteristic.

17. The measuring device as recited in claim 16, wherein:
the nonlinear varying characteristic is logarithmic.

18. The measuring device as recited in claim 15, further comprising:
an image memory for temporarily buffering images supplied by the one of the CCD image sensor and the CMOS image sensor.

* * * * *